United States Patent
Kato et al.

[11] Patent Number: 6,036,841
[45] Date of Patent: Mar. 14, 2000

[54] METHOD FOR MEASURING NITROGEN OXIDE

[75] Inventors: Nobuhide Kato, Ama-gun; Noriyuki Ina, Okazaki, both of Japan

[73] Assignee: NGK Insulators, Ltd., Japan

[21] Appl. No.: 08/854,746

[22] Filed: May 12, 1997

[30] Foreign Application Priority Data

May 16, 1996 [JP] Japan ................................. 8-121253
Apr. 28, 1997 [JP] Japan ................................. 9-111083

[51] Int. Cl.[7] ................................................ G01N 27/407
[52] U.S. Cl. ........................ 205/781; 204/425; 204/426; 204/427; 205/784.5; 205/785
[58] Field of Search ................... 204/421–429; 205/783.5, 784, 784.5, 785, 781

[56] References Cited

U.S. PATENT DOCUMENTS

| | | | |
|---|---|---|---|
| 4,927,517 | 5/1990 | Mizutani et al. | 204/410 |
| 5,034,112 | 7/1991 | Murase et al. | 204/410 |
| 5,145,566 | 9/1992 | Logothetis et al. | 204/424 |
| 5,217,588 | 6/1993 | Wang et al. | 204/426 |
| 5,397,442 | 3/1995 | Wachsman | 204/425 |
| 5,672,811 | 9/1997 | Kato et al. | 204/425 |

FOREIGN PATENT DOCUMENTS

| | | |
|---|---|---|
| 0 127 964 A2 | 12/1984 | European Pat. Off. . |
| 0 517 366 A1 | 12/1992 | European Pat. Off. . |
| 0 678 740 A1 | 10/1995 | European Pat. Off. . |
| 0678740 | 10/1995 | European Pat. Off. . |
| 2 288 873 | 11/1995 | United Kingdom . |
| 95/30146 | 11/1995 | WIPO . |

OTHER PUBLICATIONS

Database WPI, Section Ch, Week 9303, Derwent Publications Ltd., London, GB; Class H06, AN 93–021928 XP002037295 & JP 04 348 268 A (Japan Electronic Control System), Dec. 3, 1992, *abstract*; and Patent Abstracts of Japan, vol. 17, No. 207 (P–1525), Apr. 22, 1993.

*Primary Examiner*—T. Tung
*Attorney, Agent, or Firm*—Parkhurst & Wendel, L.L.P.

[57] ABSTRACT

A method for measuring nitrogen oxide (NOx) in a gas by decomposing NOx in the gas and measuring an amount of oxygen generated by the decomposition includes: introducing the gas to a first inner space under a first diffusion resistance and connected with an external space, controlling an oxygen partial pressure in an atmosphere in the first inner space to be a predetermined low value at which NO is not decomposed substantially by a main pump means, introducing a controlled atmosphere of the first inner space into a second inner space which is connected with the first inner space and which is under a second diffusion resistance, and converting the atmosphere into an electric signal corresponding to the quantity of oxygen generated by decomposition or reduction of NOx contained in the atmosphere by an electric signal conversion means. A first oxygen concentration detecting means is disposed for detecting an oxygen partial pressure in the second inner space, and a control voltage to be applied to the main pump means is adjusted on the basis of an output of the first oxygen concentration detecting means.

7 Claims, 7 Drawing Sheets

METHOD FOR MEASURING NITROGEN OXIDE

BACKGROUND OF THE INVENTION AND RELATED ART STATEMENT

The present invention relates to a method for measuring nitrogen oxide. Particularly, the present invention provides a method for measuring a very small amount of nitrogen oxide in a gas containing a great amount of interfering gas with a high preciseness.

With regard to a method for obtaining NOx amount in a gas to be measured by measuring an amount of oxygen generated by decomposing NOx in the gas to be measured, there has conventionally been, for example, a method disclosed in European Patent Laid Open No. 0678740A1 as shown in FIG. 13.

In FIG. 13, 80 is a NOx sensor having a main pump means 60 and an electric signal conversion means 70. The main pump means 60 includes an electrochemical pump cell 6 comprising a substrate 3 comprising an oxygen ion conductive solid electrolyte and an inner pump electrode 5 and an outer pump electrode 4 formed on the inner surface and outer surface of the substrate, respectively. The main pump means 60 treats oxygen contained in the measuring gas introduced from an external space by pumping processing on the basis of a control voltage applied between the inner pump electrode 5 and the outer pump electrode 4 by a power source 7. The electric signal conversion means 70 includes a pair of detection electrodes 11 and 14 formed on the side where the measuring gas that was treated by pumping processing by the main pump means is introduced. The electric signal conversion means 70 generates an electric signal corresponding to the quantity of oxygen generated by decomposition or reduction of NOx contained in the measuring gas after treated by the pumping processing by the main pump means 60.

There has conventionally been used the NOx sensor 80 for measuring an amount of nitrogen oxide in a gas by introducing the gas to a first inner space 2 connected with the external space by means of a first diffusion resistance 1, controlling an oxygen partial pressure in an atmosphere in the first inner space 2 to be a predetermined low value at which NO is not decomposed substantially by the main pump means 60, introducing a controlled atmosphere of the first inner space 2 into a second inner space 9 connected with the first inner space 2 by means of a second diffusion resistance 8, and converting the atmosphere into an electric signal corresponding to the quantity of oxygen generated by decomposition or reduction of NOx contained in the atmosphere by the electric signal conversion means 70.

Incidentally, in FIG. 13, a potential difference detection means 40 measures an electromotive force V1 corresponding to a difference in oxygen partial pressure between an electrode 10 exposed in the first inner space 2 and an electrode 11 exposed in a space 15 where a standard gas is present. A voltage applied to the main pump means 60 is adjusted so that the electromotive force V1 is controlled to have a predetermined value.

However, it is difficult by this method to completely remove an influence of an interfering gas, for example, oxygen gas, carbonic acid gas, steam, or the like, in an exhaust gas of an internal engine. Because of a difference between a gas concentration in the side facing the first inner space 2 of an inner pump electrode 5 of the electrochemical pump cell 6 and that in the side of the outer pump electrode 4, a disorder of an atmosphere in the first inner space 2 by pulsation of a gas to be measured, an error caused by decomposition of water, a change of electrode activity or diffusivity of each gas component with a change of a temperature of a sensor element, a change of standing of electrodes and electrolyte, a discordance between an average value of an electrode potential of the electrochemical pump cell 6 and an average of a gas concentration, etc., it was difficult to maintain an oxygen partial pressure of a gas introduced into the second inner space 9 to be a certain value. When NOx in a gas having a high oxygen partial pressure is measured, an oxygen partial pressure of a gas introduced into the second inner space 9 is changed to be higher. According to the change, a base line of an electric signal (a pump current value Ip in FIG. 13) by an electric signal conversion means 70 corresponding to NOx amount is also changed. Particularly, it causes a large error when a very small amount of NOx is measured. On the contrary, when a steam amount of a gas to be measured increases, a hydrogen amount in the first inner space 2 in an equilibrium condition, a balance between hydrogen and oxygen in the second inner space 9 is lost by the difference in diffusion coefficients, a part of oxygen generated by decomposition of NOx is consumed by combining with hydrogen, thereby causing an error in measuring NOx.

SUMMARY OF THE INVENTION

The present invention solves the problems of a conventional measuring method and aims to provide a highly precise method for measuring an nitrogen oxide in a gas, the method has little influence of a concentration of oxygen or steam in the gas and little fluctuation by a temperature change.

According to the present invention, there is provided a method for measuring nitrogen oxide (NOx) in a gas by decomposing NOx in the gas and measuring an amount of oxygen generated by the decomposition, using a sensor comprising:

a main pump means including an electrochemical pump cell comprising a substrate comprising an oxygen ion conductive solid electrolyte and an inner pump electrode and an outer pump electrode formed on the inner surface and outer surface of the substrate, respectively, and the main pump means treating oxygen contained in the measuring gas introduced from an external space by pumping processing on the basis of a control voltage applied between the inner pump electrode and the outer pump electrode, and an electric signal conversion means for generating an electric signal corresponding to the quantity of oxygen generated by decomposition or reduction of NOx contained in the measuring gas after treated by the pumping processing by the main pump means in which one side thereof has a pair of detection electrodes formed on the side where the measuring gas that was treated by pumping processing by the main pump means is introduced;

the method for measuring nitrogen oxide (NOx) comprising the steps of:

introducing the gas to a first inner space under a first diffusion resistance and connected with the external space, controlling an oxygen partial pressure in an atmosphere in the first inner space to be a predetermined low value at which NO is not decomposed substantially by the main pump means, introducing a controlled atmosphere of the first inner space into a second inner space which is connected with the first inner space and which is under a second diffusion resistance, and converting the atmosphere into an electric signal corresponding to the quantity of oxygen generated by decomposition or reduction of NOx contained in the atmosphere by the electric signal conversion means;

wherein a first oxygen concentration detecting means is disposed for detecting an oxygen partial pressure in the second inner space, and a control voltage to be applied to the main pump means is adjusted on the basis of an output of the first oxygen concentration detecting means.

According to the present invention, there is further provided a method for measuring nitrogen oxide (NOx) in a gas by decomposing NOx in the gas and measuring an amount of oxygen generated by the decomposition, using a sensor comprising:

a main pump means including an electrochemical pump cell comprising a substrate comprising an oxygen ion conductive solid electrolyte and an inner pump electrode and an outer pump electrode formed on the inner surface and outer surface of the substrate, respectively, and the main pump means treating oxygen contained in the measuring gas introduced from an external space by pumping processing on the basis of a control voltage applied between the inner pump electrode and the outer pump electrode, and an electric signal conversion means for generating an electric signal corresponding to the quantity of oxygen generated by decomposition or reduction of NOx contained in the measuring gas after treated by the pumping processing by the main pump means in which one side thereof has a pair of detection electrodes formed on the side where the measuring gas that was treated by pumping processing by the main pump means is introduced;

the method for measuring nitrogen oxide (NOx) comprising the steps of:

introducing the gas to a first inner space under a first diffusion resistance and connected with the external space, controlling an oxygen partial pressure in an atmosphere in the first inner space to be a predetermined low value at which NO is not decomposed substantially by the main pump means, introducing a controlled atmosphere of the first inner space into a second inner space which is connected with the first inner space and which is under a second diffusion resistance, and converting the atmosphere into an electric signal corresponding to the quantity of oxygen generated by decomposition or reduction of NOx contained in the atmosphere by the electric signal conversion means;

wherein a second oxygen concentration detecting means is positioned in a third inner space connected with the first inner space by means of a third diffusion resistance, and a control voltage to be applied to the main pump means is adjusted on the basis of an integral value of an output of the second oxygen concentration detecting means.

In a sensor having the aforementioned structure, it is not necessary to keep an atmosphere of the first inner space constant. The atmosphere of the first inner space is controlled only to keep constant an atmosphere of a peripheral portion of an entrance of the second inner space. Accordingly, a change of a composition of a gas to be measured is roughly dealt with by controlling a voltage by the main pump means or a feedback control (a proportional control and/or a differential control) by an oxygen concentration detecting means arranged in the first inner space. To a small declination for a relatively long period of time, the voltage applied to the main pump means is controlled with using an output by a means for detecting an atmosphere in the peripheral portion of an entrance of the second inner space. An oxygen partial pressure of the second inner space relates to a substantially integrated value of an atmosphere of the first space for a predetermined period of time by a diffusion resistance of the entrance of the second inner space and a capacity of the second inner space. When an integrated value taken for the longer period of time is required, it is desirable to integrate an output of an oxygen concentration detecting means by an electric circuit.

All influences of factors of various changes can be compensated by controlling an atmosphere in the peripheral portion of the entrance of the second inner space, which makes a very stable measurement with a high precision possible.

Incidentally, an electric signal conversion means is an electrochemical pump cell or an electrochemical sensor cell in the present invention.

DETAILED DESCRIPTION OF THE PREFERRED EMBODIMENT

Figure 1:
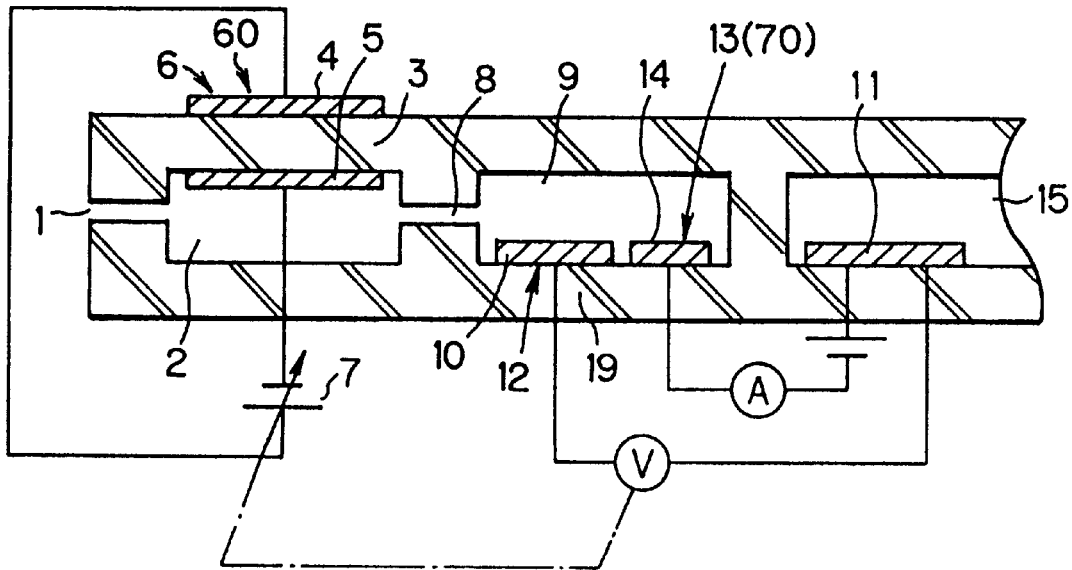
FIG. 1 is an explanatory view showing an embodiment of a basic constitution of a sensor used for a method of the present invention.
Figure 2:
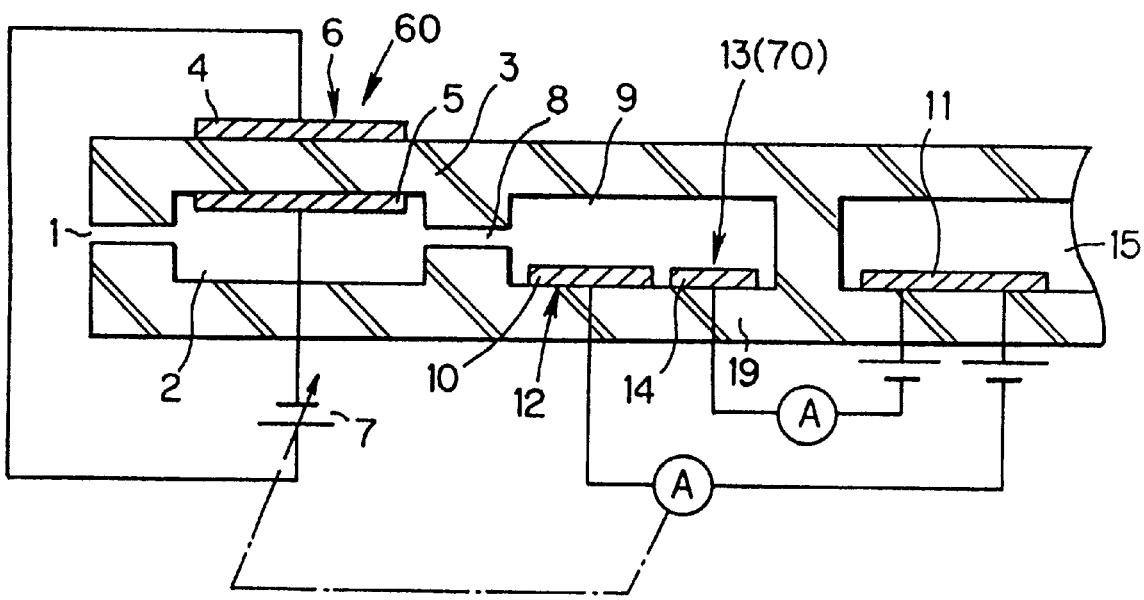
FIG. 2 is an explanatory view showing another embodiment of a basic constitution of a sensor used for a method of the present invention.
Figure 3:
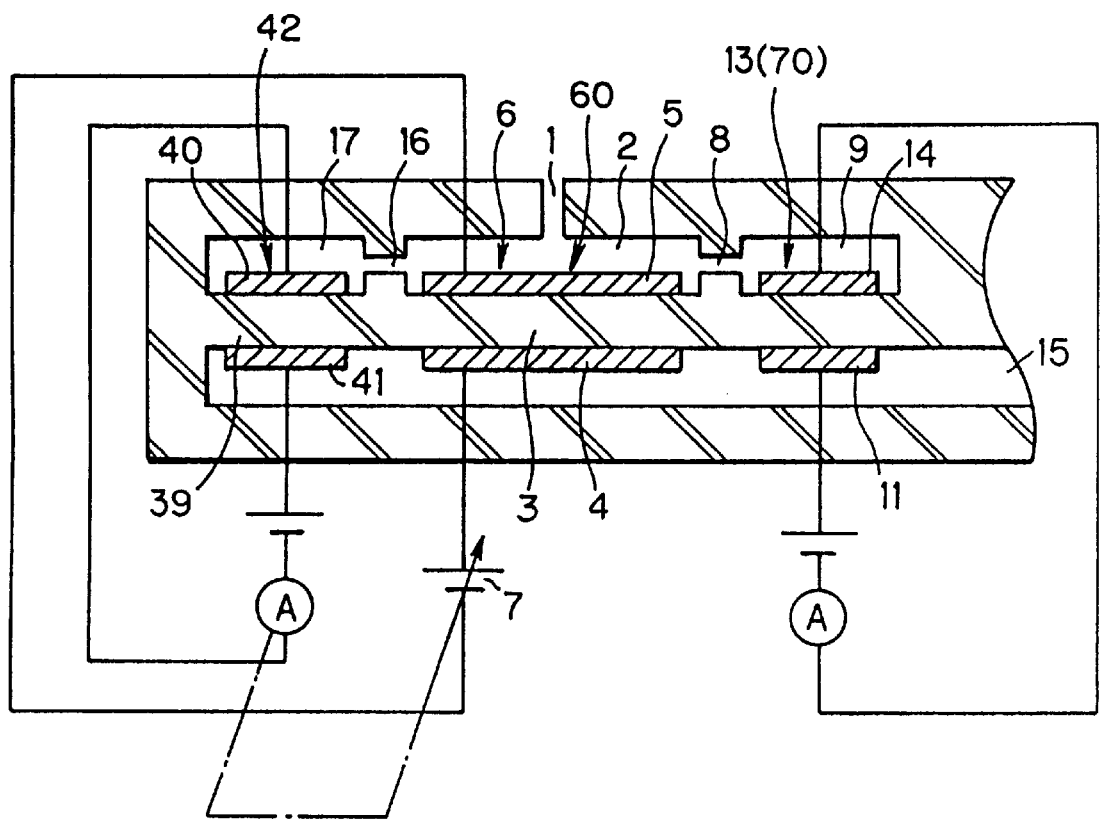
FIG. 3 is an explanatory view showing still another embodiment of a basic constitution of a sensor used for a method of the present invention.

FIGS. 1, 2, and 3 are explanatory views each showing a basic constitution of a sensor used for a method of the present invention.

In FIG. 1, a gas containing a nitrogen oxide and oxygen which interferes the nitrogen oxide is introduced into a first inner space 2 through a first diffusion resistance 1. A main pump means 60 includes an electrochemical cell 6 having a first oxygen ion conductive solid electrolyte 3 such as zirconia and a pair of inner and outer pump electrodes 5 and 4, respectively. The inner electrode 5 of the electrochemical cell 6 is exposed in the first inner space 2. A control voltage is applied to the electrochemical cell 6 from a power source 7, thereby controlling an atmosphere in the first inner space 2 so as to contain little oxide. At this time, the first inner space 2 may be provided with a pair of electrochemical cells (not shown) so as to control the atmosphere since a voltage applied to the electrochemical pump cell 6 is controlled by an output of the electrochemical cells.

Almost all oxygen (interfering component) is removed from a gas to be measured in such a manner. The gas is introduced into a second inner space 9 through a second diffusion resistance 8. An electrochemical cell 12 is an oxygen concentration detecting means having a second oxygen ion conductive solid electrolyte 19 such as zirconia and a pair of electrodes 10 and 11. The electrode 10 is exposed in the second inner space 9. The output of the electrochemical cell 12 is fed back to a power source 7 which applies the output of the electrochemical cell 12 to the electrochemical pump cell 6 so that a value of an electromotive force V1 of the electrochemical cell 12 coincides with a predetermined value. Accordingly, an oxygen partial pressure in the second inner space 9 is less influenced by a composition of a gas to be measured in comparison with the case in which the output is controlled only by signals in the first inner space 2.

Thus obtained gas to be measured in the second inner space 9, for example, nitrogen monoxide, is decomposed as shown by the following formula by a catalytic action or a reducing action by electrification on a detection electrode 14 of the electrochemical pump cell 13 which is an electric signal conversion means 70, the detection electrode 14 being exposed in the second inner space 9. As a result, a generated oxygen is sent to a space 15 where a standard gas is present through the detection electrode 14 and a reference electrode 11. An amount of NOx is obtained by a value of a current generated by the transference of the oxygen.

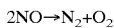

2NO→N$_2$+O$_2$    [Formula 1]

FIG. 2 shows an embodiment in which an oxygen concentration detecting means formed in the second inner space 9 is an oxygen pump by an electrochemical cell 12. The others are the same as in FIG. 1. In FIG. 2, an oxygen partial pressure in the second inner space 9 is detected as a limited diffusion current by a predetermined voltage applied to the portion between the electrode 10 and the electrode 11. The output is fed back to the power source 7 which applies the output to the first electrochemical cell 6 so that a value of the limited diffusion current coincides with a predetermined value.

FIG. 3 shows a constitution in which an oxygen concentration detecting means is set up in the third inner space which is different from the second inner space.

A gas to be measured is introduced into the first inner space 2 through the first diffusion resistance 1.

As in the embodiment shown in FIG. 1, an inner pump electrode 5 of a main pump means 60 having an electrochemical pump cell 6 is exposed in the first inner space 2. The electrochemical pump cell 6 has a first oxygen ion conductive solid electrolyte 3 such as zirconia and a pair of inner and outer pump electrodes 5 and 4, respectively. A control voltage is applied to the electrochemical pump cell 6 from a power source 7, thereby controlling an atmosphere in the first inner space 2 so as to contain little oxide. After almost all oxygen in the gas is removed from the gas in the first inner space 2, the gas is introduced to the third inner space 17 through the third diffusion resistance 16. The diffusion resistance 16 and the third inner space 17 desirably have structures almost same as those of the second diffusion resistance 8 and the second inner space 9, respectively, so as to make both atmospheres close to each other.

As in FIGS. 1 and 2, an electrochemical cell 42 is an oxygen concentration detecting means having an oxygen ion introducing solid electrolyte 39 such as zirconia and a pair of electrodes 40 and 41. The electrode 40 is exposed in the third inner space 17. The output of the electrochemical cell 42 is fed back to a power source 7 which applies the output of the electrochemical cell 42 to the electrochemical pump cell 6 so that a value of a limited diffusion current generated by a predetermined voltage applied to the electrodes 40 and 41 of the cell 42 coincides with a predetermined value.

On the other hand, after almost all oxygen was removed from the gas to be measured in the first inner space 2, the gas is introduced to the second inner space 9 through the second diffusion resistance 8. In the gas introduced in the second inner space 9, oxygen is generated by a catalytic action or a reducing action by electrification on a detection electrode 14 of the electrochemical pump cell 13 which is an electric signal conversion means 70, the detection electrode 14 being exposed in the second inner space 9. As a result, the oxygen is sent to a space 15 where a standard gas is present through the detection electrode 14 and a reference electrode 11. An amount of NOx is obtained by a value of a current generated by the transference of the oxygen.

Figure 4:
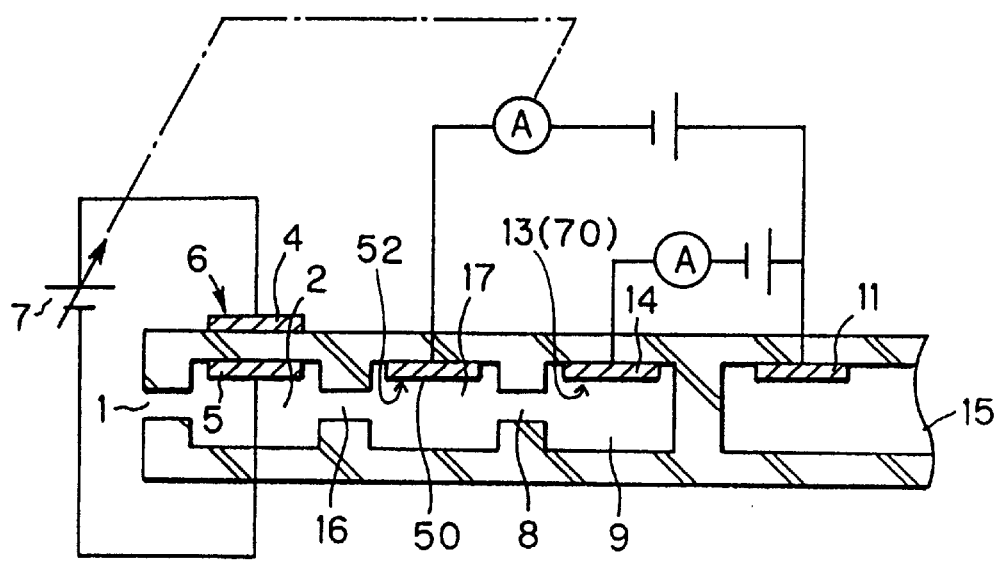
FIG. 4 is an explanatory view showing yet another embodiment of a basic constitution of a sensor used for a method of the present invention.

FIG. 4 shows a constitution in which the second inner space is connected to the first inner space by means of the third inner space.

A gas to be measured is introduced in the third inner space 17 through the third diffusion resistance 16. Almost all oxygen in the gas is removed from the gas here. The gas is introduced into the third inner space 17 through the third diffusion resistance 16. An atmosphere in the third inner space 17 is controlled to be close to a predetermined atmosphere by an electrochemical cell 52 which is an oxygen concentration detecting means. Simultaneously, the output is fed back to a power source 7 which applies a control voltage to the electrochemical pump cell 6 so that an oxygen content in the third inner space 17 is controlled more precisely. Thus, an oxygen partial pressure of the gas to be measured is precisely controlled. The gas enters the second inner space 9 through the second diffusion resistance 8. Oxygen is generated by a catalytic action or a reducing action by electrification on a detection electrode 14 of the electrochemical pump cell 13 which is an electric signal conversion means 70, the detection electrode 14 being exposed in the second inner space 9. As a result, the oxygen is sent to a space 15 where a standard gas is present through the detection electrode 14 and a reference electrode 11. An amount of NOx is obtained by a value of a current generated by transference of the oxygen.

Figure 5:
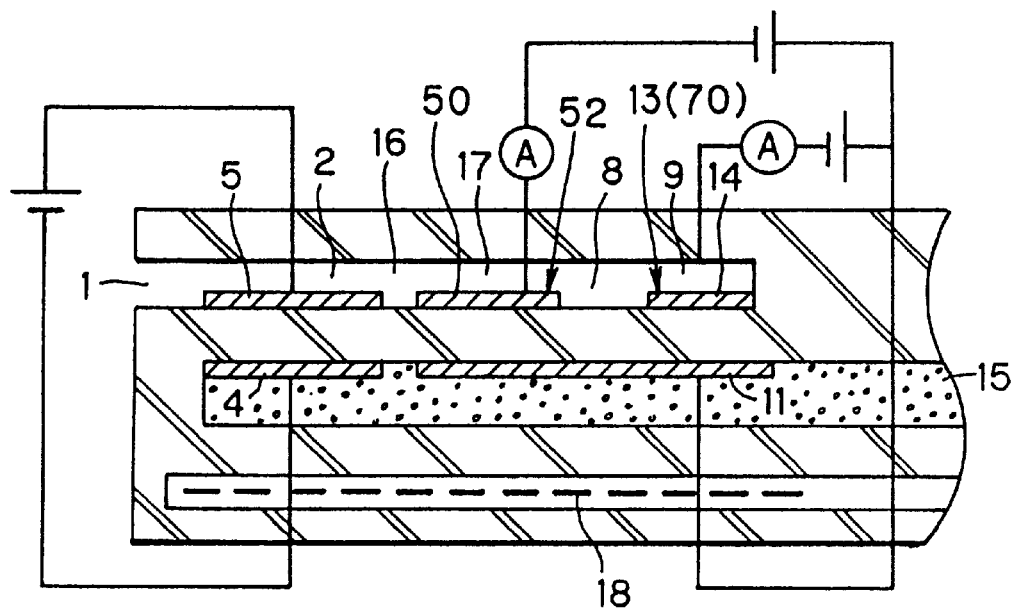
FIG. 5 is an explanatory view of a principal part of the embodiment of a constitution shown in FIG. 4.

FIG. 5 is an embodiment of the constitution shown in FIG. 4. The first diffusion resistance 1, the first inner space 2, the third diffusion resistance 16, the third inner space 17, the second diffusion resistance 8, and the second inner space 9 are arranged in a line as a flat and narrow opening. Since the constitution enables the inner spaces formed in a sensor to have a small capacity, the constitution can give a high response speed. Incidentally, a space 15 where a standard gas is present is filled with a porous ceramics, and a strength of a sensor element is improved there. A heater 18 is embedded in the sensor element, and the sensor element is heated at a predetermined temperature.

Figure 6:
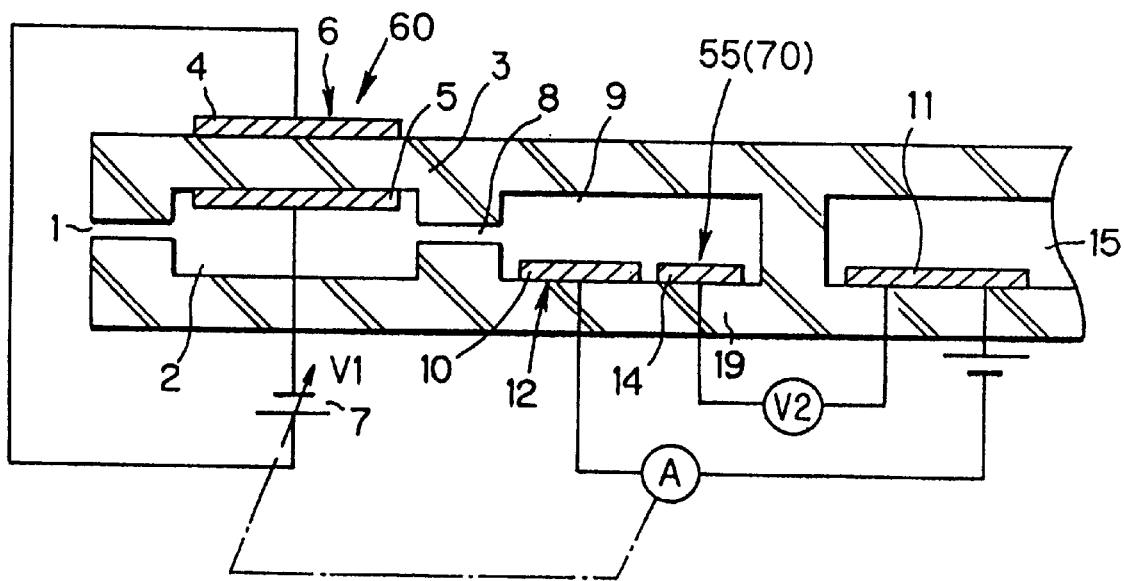
FIG. 6 is an explanatory view showing yet another embodiment of a basic constitution of a sensor used for a method of the present invention.

FIG. 6 shows an embodiment in which the electrochemical pump cell 13 of a constitution shown in FIG. 2 is substituted by an electrochemical sensor cell 55 as an electric signal conversion means 70. The others are the same as in FIG. 2. Accordingly, when a sensor having a structure shown in FIG. 6 is used, a gas to be measured in a second inner space 9 is generated by a catalytic action on a detection electrode 14 of the electrochemical sensor cell 55 which is an electric signal conversion means 70, the detection electrode 14 being exposed in the second inner space 9. As a result, an amount of NOx is obtained from an electromotive force generated between a detection electrode 14 and a reference electrode 11.

Figure 7:
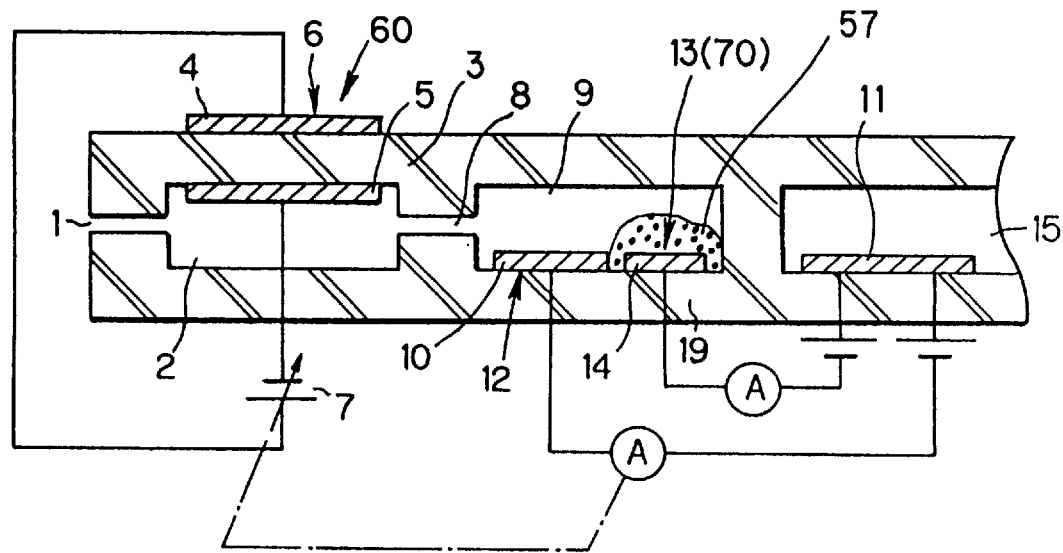
FIG. 7 is an explanatory view showing yet another embodiment of a basic constitution of a sensor used for a method of the present invention.

FIG. 7 shows an embodiment in which a porous protective layer 57 was disposed on a detection electrode 14 in a constitution shown in FIG. 2. In this embodiment, a second inner space 9 and a second diffusion resistance 8 are formed with using a porous body. The other constitutions are the same as in FIG. 2.

In such a constitution of a sensor element, the second inner space 9 and the second diffusion resistance 8 may be unitarily formed with using a porous ceramic and disposed in a third inner space 17.

Further, the second inner space 9 and the second diffusion resistance 8 may be substituted by adjustment of porosity (rate of pores, diameter of pores, etc.) of an electrode 14 of signal conversion means 70 which is exposed in a gas to be measured.

In FIG. 7, it is possible to unitarily form the second inner space 9 and the second diffusion resistance 8 with using a porous ceramic and dispose them in a first inner space 2. Alternatively, the second inner space 9 and the second diffusion resistance 8 may be substituted by adjustment of porosity (rate of pores, diameter of pores, etc.) of an electrode 14 of signal conversion means 70 which is exposed in a gas to be measured.

Figure 8:
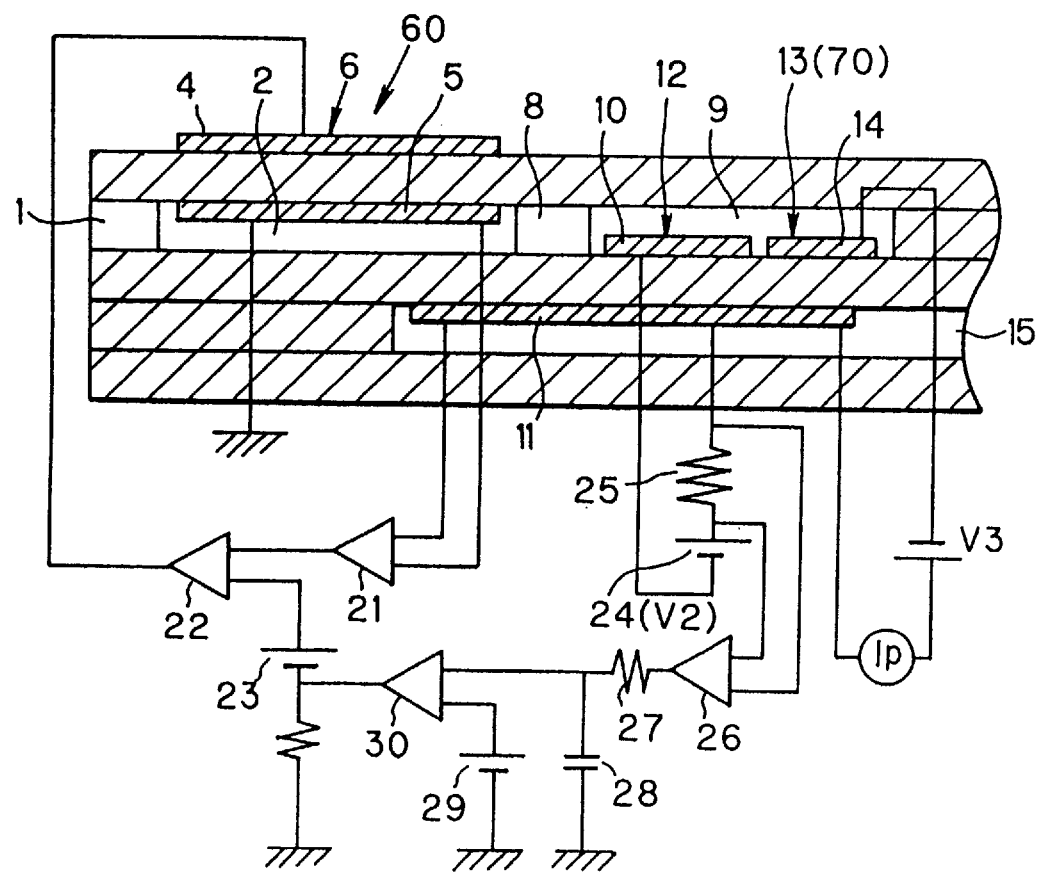
FIG. 8 is a cross-sectional view and a circuit showing an embodiment of a sensor to be used in the present invention.

FIG. 8 shows an embodiment of a measuring circuit of the present invention. A gas to be measured is introduced into a first inner space 2 through a first diffusion resistance 1. There, almost all oxygen in the gas is removed by an electrochemical pump cell 6 (main pump means 60). As a control voltage applied between an outer pump electrode 4 and an inner pump electrode 5 of the electrochemical pump cell 6, an output compared with a predetermined voltage of a power source 23 by a comparator 22 is used with an electromotive force between the inner pump electrode 5 and a reference electrode 11 being subjected to an impedance conversion by an amplifier 21. The gas to be measured obtains an oxygen partial pressure almost same as a predetermined one by this. The gas enters a second inner space 9 through a second diffusion resistance 8.

A predetermined voltage is applied to a electrochemical cell 12 which is an oxygen concentration detection means disposed in the second inner space 9 from a power source 24. A pump current flowing at that time is detected by a resistance 25 and an amplifier 26, made to pass an integrated circuit of a resistance 27 and a condenser 28, and compared with a predetermined volume of a power source 29 by a comparator 30. A voltage to be applied to the electrochemical pump cell 6 is adjusted by the output. An atmosphere in the second inner space 9 is stabilized by this. NOx is decomposed by an electrode 14 having a catalytic activity, and an amount of generated oxygen is detected as a pump current of an electrochemical pump cell 13.

Incidentally, an oscillation of the aforementioned integrated circuit can be avoided by setting a time constant for an adequate value. The inner pump electrode 5 in the first inner space 2 and the electrode 10 in the second inner space 9 are preferably made of a material having a low catalytic activity to NOx, for example, Au or Au-Pt alloy. The electrode 14 which detects NOx is preferably made of a material having a high catalytic activity to NOx such as Rh.

[EXAMPLE]

Figure 13:
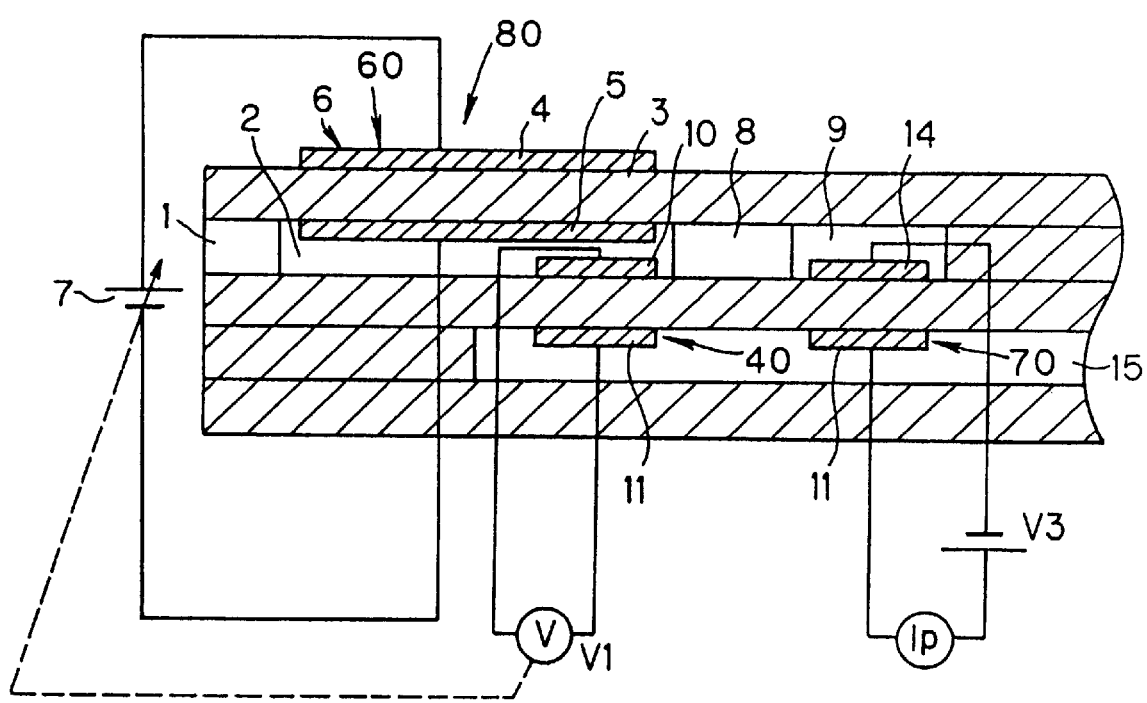
FIG. 13 is an explanatory view showing an embodiment of a constitution of a conventional sensor.

In each of the case of the sensor and circuit shown in FIG. 8, in which a zirconia porcelain was used as a solid electrolyte, and the case of the conventional sensor and circuit shown in FIG. 13, an exhaust gas of a gasoline-combustion engine was measured for NOx amount therein. A change of pump current values of the electric signal conversion means 70 (electrochemical pump cell 13) according to a concentration of an interfering gas component in the exhaust gas was compared to each other.

Figure 9:
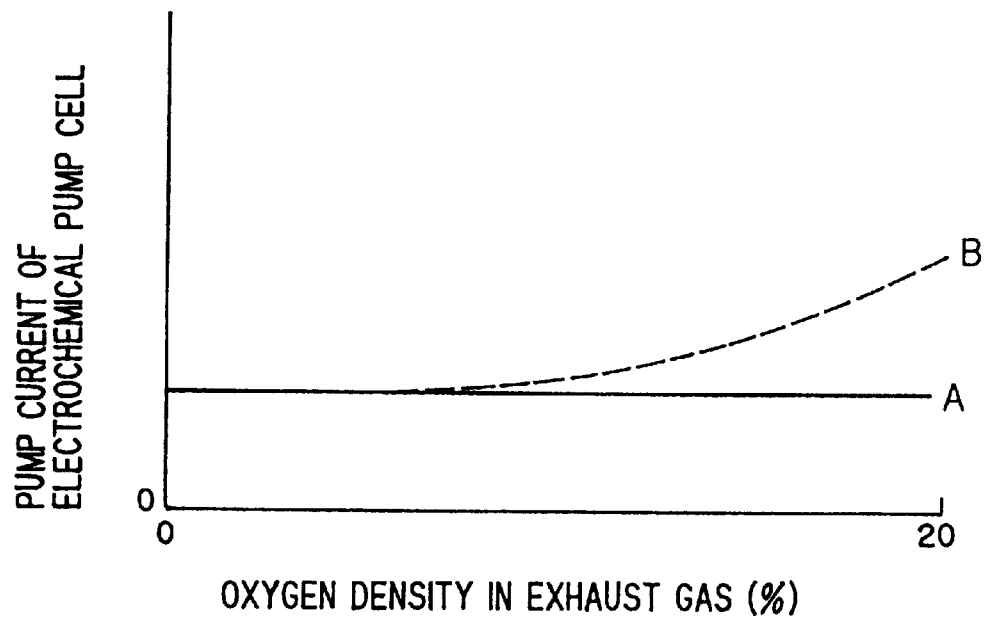
FIG. 9 is a graph showing a comparison of a change of pump current values of an electrochemical pump cell corresponding to an oxygen partial pressure in an exhaust gas by a method of the present invention and a conventional method.
Figure 10:
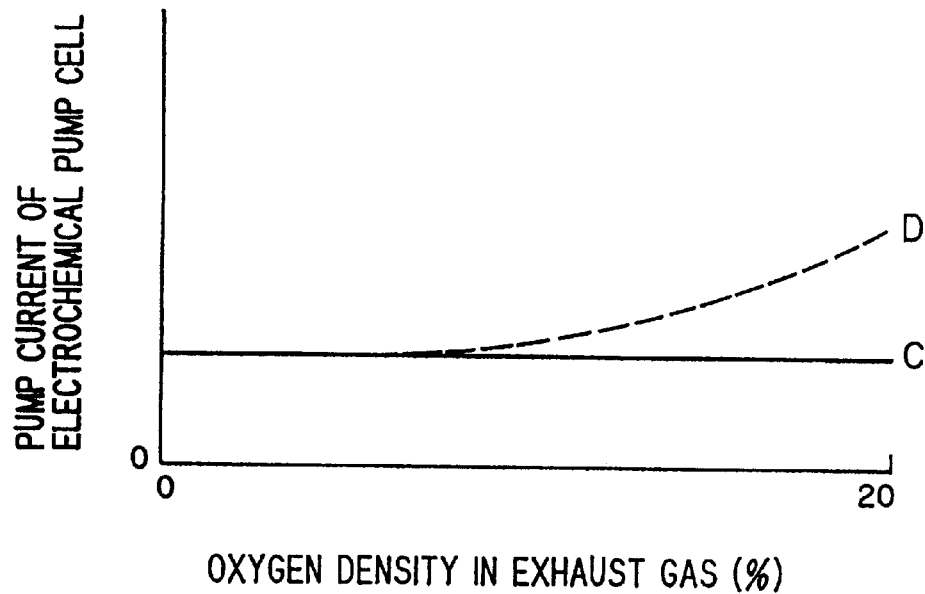
FIG. 10 is a graph showing a comparison of a change of pump current values of an electrochemical pump cell corresponding to an oxygen partial pressure in an exhaust gas by a method of the present invention and a conventional method.
Figure 11:
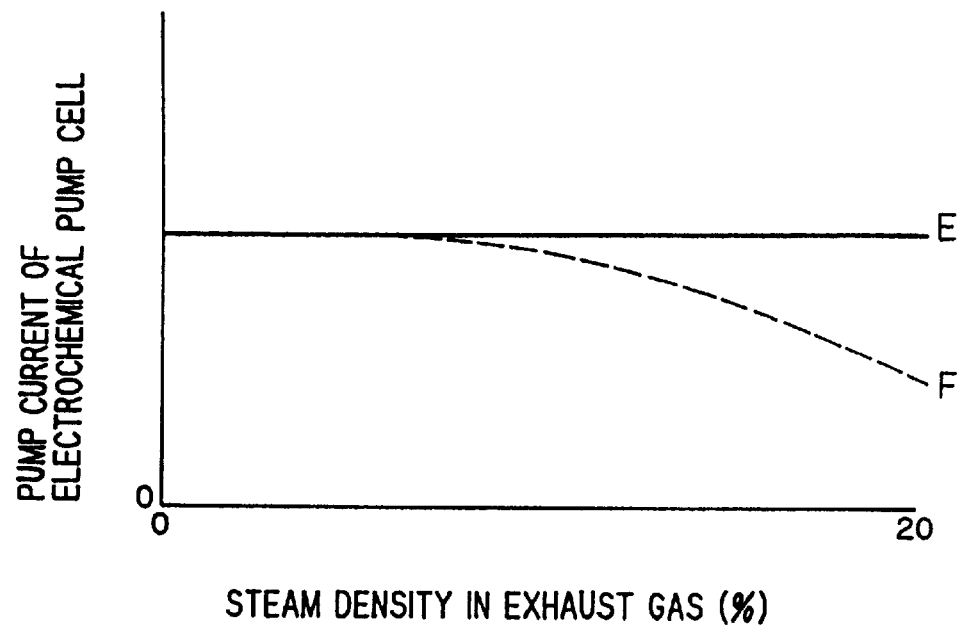
FIG. 11 is a graph showing a comparison of a change of pump current values of an electrochemical pump cell corresponding to a steam concentration in an exhaust gas by a method of the present invention and a conventional method.

A voltage V1 between the inner pump electrode 5 and the reference electrode 11, a terminal voltage V2 at the electrochemical cell 12, and a terminal voltage V3 at the electrochemical pump cell 13 were adjusted as in Table 1. The results are shown in FIGS. 9–11.

Incidentally, FIG. 13 shows a sensor in which an oxygen partial pressure in the first inner space 2 is controlled only by a potential difference detection means 40. One of the electrodes of the potential difference detection means 40 is exposed in the first inner space 2.

TABLE 1

|    | Example 1 (FIG. 9) | Example 2 (FIG. 10) | Example 3 (FIG. 11) |
|----|--------------------|--------------------|--------------------|
| V1 | 300 mV             | 300 mV             | 300 mV             |
| V2 | 400 mV             | 400 mV             | 400 mV             |
| V3 | 450 mV             | 430 mV             | 430 mV             |

As FIG. 9 shows, when an oxygen partial pressure in a gas to be measured ascended, a pump current flowing in the electric signal conversion means (electrochemical pump cell) 70 was increased as a curved line B in a measuring method having a conventional constitution shown in FIG. 13, thereby increasing an error. On the other hand, in a straight line A based on a method of the present invention shown in FIG. 8, an oxygen partial pressure dispersed in the second inner space 9 is detected and negatively fed back to the electrochemical pump cell 6. Accordingly, a pump current flowing in the electric signal conversion means 70 (electrochemical pump cell 13) is not changed even if an oxygen partial pressure in a gas to be measured changes. Thus, a measuring preciseness (a change of an offset current) is sharply improved. However, since there is a large difference between an electromotive force and an applied voltage V3 of the electric signal conversion means in this embodiment, an offset value of the pump current is not zero.

In FIG. 10, when an oxygen partial pressure in a gas to be measured in the conventional constitution shown in FIG. 13 ascended, a pump current flowing in the electric signal conversion means (electrochemical pump cell) 70 was increased as shown by a curved line D, thereby increasing an error. On the other hand, in the method of the present invention shown in FIG. 8, a pump current flowing in the electric signal conversion means 70 (electrochemical pump cell 13) is not changed as shown by a straight line C even if an oxygen partial pressure in a gas to be measured changes. Further, an electromotive force of the electric signal conversion means was equalized with an applied voltage V3 when an oxygen partial pressure in the gas to be measured was zero. As a result, an offset value of a pump current of the electric signal conversion means was zero at that time.

As FIG. 11 shows, when a steam concentration in a gas to be measured ascended in a conventional constitution shown in FIG. 13, a pump current flowing in the electric signal conversion means (electrochemical pump cell) 70 was decreased as a curved line F, thereby increasing an error. The reason seems that because a diffusion coefficient of hydrogen generated by dissociation of water in the first inner space 2 is larger than that of oxygen, hydrogen enters the second inner space 9 more than the oxygen. Accordingly, an equilibrium oxygen partial pressure in the second inner space is lowered, and a pump current required for maintaining a predetermined oxygen partial pressure in the second inner space 9 is decreased.

On the other hand, in a method of the present invention shown in FIG. 8, since the electrochemical cell 12 plays a part of adjustment including a difference in diffusion coefficients based on a difference in kinds of gases or a temperature change in the second diffusion resistance 8, a pump current flowing in the electric signal conversion means 70 (electrochemical pump cell 13) is not changed as a straight line E even if an oxygen partial pressure in a gas to be measured changes.

Then, in each of the case of the sensor and circuit shown in FIG. 6 (present invention), in which a zirconia porcelain was used as a solid electrolyte, and the case of the conventional sensor and circuit shown in FIG. 13, an exhaust gas of a gasoline-combustion engine was measured for NOx amount therein in the same manner as described above. A change of electromotive force of the electric signal conversion means 70 (electrochemical sensor cell 55) according to a oxygen partial pressure in the exhaust gas was compared to each other. Incidentally, in a sensor shown in FIG. 13, the electrochemical pump cell was substituted by an electrochemical sensor cell as the electric signal conversion means 70.

Incidentally, in FIG. 6 (present invention), V1 and V2 were set to be 300 mV and 400 mV, respectively. In FIG. 13 (conventional method) V1 was set to be 300 mV. The results are shown in FIG. 12.

Figure 12:
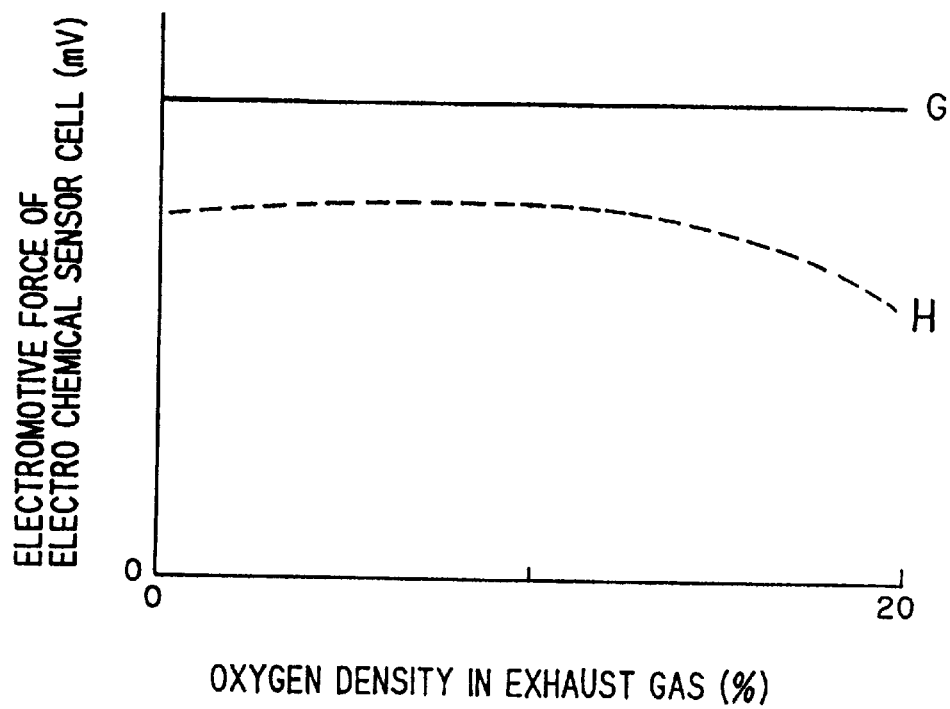
FIG. 12 is a graph showing a comparison of a change of electromotive force of an electrochemical sensor cell corresponding to an oxygen partial pressure in an exhaust gas by a method of the present invention and a conventional method.

As FIG. 12 shows, when an oxygen partial pressure in a gas to be measured in the conventional constitution shown in FIG. 13 ascended, an electromotive force in the electric signal conversion means (electrochemical sensor cell) 70 was decreased as shown by a curved line H, thereby increasing an error. On the other hand, in the method of the present invention shown in FIG. 6, an electromotive force in the electric signal conversion means 70 (electrochemical sensor cell 55) is not changed as shown by a straight line G even if an oxygen partial pressure in a gas to be measured changes. Accordingly, NOx can be measured very precisely.

As obvious from the above description, the present invention gives a very precise method for measuring NOx, having little influence of oxygen or steam concentration in a gas to be measured and little fluctuation by a temperature change, and is very useful as a means for improving an air environment, or the like.

What is claimed is:

1. A method for measuring nitrogen oxide (NOx) in a gas by decomposing NOx in the gas and measuring an amount of oxygen generated by the decomposition, using a sensor comprising:

a main pump means including an electrochemical pump cell comprising a substrate comprising an oxygen ion conductive solid electrolyte and an inner pump electrode and an outer pump electrode formed on the inner surface and outer surface of the substrate, respectively, and said main pump means treating oxygen contained in the measuring gas introduced from an external space by pumping processing on the basis of a control voltage applied between said inner pump electrode and said outer pump electrode, and an electric signal conversion means for generating an electric signal corresponding to the quantity of oxygen generated by decomposition or reduction of NOx contained in the measuring gas after having been treated by the pumping processing by said main pump means, said electric signal conversion means having a pair of detection electrodes where one of the electrodes is on the side where the measuring gas that was treated by pumping processing by said main pump means is introduced;

said method for measuring nitrogen oxide (NOx) comprising the steps of:

introducing the gas to a first inner space under a first diffusion resistance and connected with said external space, controlling an oxygen partial pressure in an atmosphere in the first inner space to be a predetermined low value at which NO is not decomposed substantially by said main pump means, introducing a controlled atmosphere of the first inner space into a second inner space which is connected with the first inner space and which is under a second diffusion resistance, detecting an oxygen partial pressure in said second inner space with an electrochemical pump cell which is located for detecting an oxygen partial pressure in the second inner space, adjusting said control voltage applied in said main pump cell in dependence on the measurement output of said electrochemical pump cell to maintain the measurement output of said electrochemical pump cell constant, and generating an electric signal corresponding to the quantity of oxygen generated by decomposition or reduction of NOx contained in said atmosphere by said electric signal conversion means.

2. A method for measuring nitrogen oxide according to claim 1, wherein said control voltage applied to the main pump means is adjusted on the basis of an integral value of an oxygen partial pressure of the second inner space for a predetermined period of time.

3. A method for measuring nitrogen oxide according to claim 1, wherein said electrochemical pump cell for detecting an oxygen partial pressure in the second inner space for controlling the oxygen partial pressure in said first inner space to be a predetermined value, has one of a pair of electrodes being exposed in the second inner space.

4. A method for measuring nitrogen oxide (NOx) in a gas by decomposing NOx in the gas and measuring an amount of oxygen generated by the decomposition, using a sensor comprising:

a main pump means including an electrochemical pump cell comprising a substrate comprising an oxygen ion conductive solid electrolyte and an inner pump electrode and an outer pump electrode formed on the inner surface and outer surface of the substrate, respectively, and said main pump means treating oxygen contained in the measuring gas introduced from an external space by pumping processing on the basis of a control voltage applied between said inner pump electrode and said outer pump electrode, and an electric signal conversion means for generating an electric signal corresponding to the quantity of oxygen generated by decomposition or reduction of NOx contained in the measuring gas after having been treated by the pumping processing by said main pump means, said electric signal conversion means having a pair of detection electrodes where one of the electrodes is on the side where the measuring gas that was treated by pumping processing by said main pump means is introduced;

said method for measuring nitrogen oxide (NOx) comprising the steps of:

introducing the gas to a first inner space under a first diffusion resistance and connected with said external space, controlling an oxygen partial pressure in an atmosphere in the first inner space to be a predetermined low value at which NO is not decomposed substantially by said main pump means, introducing a controlled atmosphere of the first inner space into a second inner space which is connected with the first inner space and which is under a second diffusion resistance, detecting an oxygen partial pressure in a third inner space, connected with the first inner space by means of a third diffusion resistance, with an electrochemical pump cell which is located for detecting an oxygen partial pressure in said third inner space, adjusting said control voltage applied in said main pump cell in dependence on the measurement output of said electrochemical pump cell to maintain the measurement output of said electrochemical pump cell constant, and generating an electric signal corresponding to the quantity of oxygen generated by decomposition or reduction of NOx contained in said atmosphere by said electric signal conversion means.

5. A method for measuring nitrogen oxide according to claim 4, wherein said control voltage applied to the main pump means is adjusted on the basis of an integral value of an oxygen partial pressure of the third inner space for a predetermined period of time.

6. A method for measuring nitrogen oxide according to claim 4, wherein said electrochemical pump cell for detecting an oxygen partial pressure in the third inner space for controlling the oxygen partial pressure in said first inner space to be a predetermined value, has one of a pair of electrodes being exposed in the third inner space.

7. A method for measuring nitrogen oxide according to claim 4, wherein the second inner space is connected to the first inner space by means of the third inner space.

* * * * *